United States Patent [19]
Luck et al.

[11] 4,250,139
[45] Feb. 10, 1981

[54] MICROWAVE STERILIZATION OF DRY PROTEIN

[75] Inventors: Edward E. Luck, Menlo Park; John R. Daniels, Portola Valley, both of Calif.

[73] Assignee: Collagen Corporation, Palo Alto, Calif.

[21] Appl. No.: 8,652

[22] Filed: Feb. 1, 1979

[51] Int. Cl.³ .................. C12N 13/00; A23L 3/10; A23L 3/16; A61L 2/12
[52] U.S. Cl. .................. 422/21; 426/234; 426/242; 435/173
[58] Field of Search .......... 422/21; 426/241, 242, 426/234; 435/173

[56] References Cited

U.S. PATENT DOCUMENTS

| | | |
|---|---|---|
| 3,031,288 | 8/1962 | Stribling et al. ............... 426/241 X |
| 3,281,332 | 10/1966 | Munns et al. ................... 422/5 X |
| 3,439,510 | 4/1969 | Gray ............................ 422/68 X |
| 3,645,849 | 2/1972 | Gray ............................ 422/21 X |
| 3,706,631 | 12/1972 | Falk ............................ 422/21 X |
| 3,743,480 | 7/1973 | Falk ............................ 422/21 |
| 3,926,556 | 12/1975 | Boscher ......................... 422/21 |

*Primary Examiner*—Barry S. Richman
*Attorney, Agent, or Firm*—Bertram I. Rowland

[57] ABSTRACT

Method for decontaminating proteinaceous host materials from microorganisms, while retaining chemical, physical and physiological properties of said host proteinaceous materials, said method comprising substantially dehydrating said host proteinaceous material, preferably by lyophilization, and subjecting said host material to a lethal dosage of microwave energy while said host material is maintained in substantially ambient conditions.

9 Claims, No Drawings

MICROWAVE STERILIZATION OF DRY PROTEIN

BACKGROUND OF THE INVENTION

1. Field of the Invention

Proteins find wide use for a variety of functions. Proteins can be used as prosthetic devices, in plastic surgery, as drugs, as blood components and the like. Since the protein can act as a nutrient source, proteins are particularly susceptible to contamination with microorganisms, such as bacteria, fungi, viruses, and the like. Furthermore, when the protein is to be introduced into a mammal, by ingestion, implantation, injection, etc., it is important that the protein be free of contaminating microorganisms. The problem that has existed for a long period of time is to find a simple way to kill the microorganisms without deleteriously affecting the chemical, physical or physiological properties of the protein.

Proteins are susceptible to variations in their environment, where their chemical, physical or physiological properties may be significantly altered. Changes in pH, ionic strength, or temperature can result in reversible or irreversible changes in the character of the protein. Treatment of the protein with chemical disinfectants or high energy radiation frequently results in substantial alterations in the nature of the protein.

It is therefore desirable to find an efficient, simple and rapid means for decontaminating, preferably sterilizing, proteinaceous materials, without alteration of the physiological properties of the host protein.

2. Description of the Prior Art

A large number of articles have described the biocidal effects of microwaves. These articles include Goldblith and Wang, Applied Microbiology, 15, 1371 (1967); Webb and Booth, Nature, 222, 1199 (1969); Cleary, American Industrial Hygiene Association Journal, 1970, 52 (Jan.-Feb.); Boucher, American Journal of Hospital Pharmacy, 29, 661 (1972); Ohlsson, et al., Journal of Microwave Power, 10, No. 1 (1975); Jasnow, et al., Applied Microbiology, 30, 205 (1975); Wayland, et al., Radiation Research, 51, 251 (1977); Latimer, et al., Journal of Clinical Microbiology, 6, 340 (1977); and Corelli, et al., Journal of Microwave Power, 12, No. 2 (1977).

A large number of patents have issued employing microwave energy for its biocidal effect, either by itself or in combination with other treatment. These patents include U.S. Pat. Nos. 3,095,359; 3,215,539; 3,261,140; 3,439,510; 3,494,723-4; 3,885,915; and 3,926,556. U.S. Pat. No. 3,858,329 teaches the use of microwave energy for drying porous materials, while U.S. Pat. No. 3,963,892 teaches the use of microwaves to heat blood samples.

SUMMARY OF THE INVENTION

Proteinaceous host materials are decontaminated or disinfected, preferably sterilized, without alteration of the physiological properties of the host material by substantially freeing the host material of water, preferably by lyophilization, and subjecting the host material to a lethal dosage of microwave energy.

DESCRIPTION OF THE SPECIFIC EMBODIMENTS

A method is provided for disinfecting, preferably sterilizing, host proteinaceous materials which are normally found, prepared or isolated in an aqueous medium, without significant alteration of the physiological property of the host material. The method comprises freeing the host material of moisture, preferably by lyophilization, and subjecting the host material to a lethal dosage of microwave energy, sufficient to kill at least a portion of the microorganisms present and preferably to kill all microorganisms.

In accordance with the subject invention, a wide variety of proteinaceous materials, which find use in the treatment of mammals, may be decontaminated or sterilized. The proteins can be any one of a wide variety of classes of proteins, such as keratins, collagens, albumins, globulins, hormones, enzymes, or the like. They can be simple proteins or conjugated proteins, such as glycoproteins, mucoproteins, lipoproteins, heme proteins, nucleoproteins, or the like. The source of the proteins can be widely varied, such as serum, skin, bone, cartilage, tendon, microorganisms, synthetic proteins, etc. The significant factor is that the protein has chemical and physical properties, which are important to its physiological function. Therefore, when decontaminating the protein, it is essential that the properties of the protein be substantially unchanged so as to retain its physiological capability.

In view of the varied characteristics of proteins, proteins are employed in a variety of ways. The proteins are used as drugs, in plasma and serum, as prosthetic devices, in surgical reconstruction, in the treatment of disorders, and the like.

In carrying out the subject invention, the protein will normally be obtained as a single or mixture of proteins in an aqueous medium. The protein is substantially dehydrated, either free of or in combination with salts, which are adventitiously present in the aqueous medium. Conveniently, the protein will be lyophilized by freezing the protein and removing the water in vacuo. Also useful means of drying are critical point drying, vacumm dehydration, and drying agents. The product is substantially water-free, preferably with all uncoordinated water removed and more preferably all water removed. The significant factor in dehydrating the protein is that the physiological properties of the protein are not significantly altered irreversibly. That is, any significant changes in the characteristics of the protein due to the dehydration are substantially reversible and the properties of the protein are substantially restored on reconstitution in an appropriate aqueous medium.

After dehydrating the protein, the protein is subjected to a lethal dosage of microwave energy. Conveniently, the protein may be contained in a container, sealed or unsealed, which is permeable to the applied microwave energy. Desirably, any container should be sterile before introducing the protein into the container for introduction into the microwave cavity. Illustrative containers included syringes, vials, plates, etc. The material of the container is desirably transparent to microwave energy in the region employed. Various materials can be employed, such as glass, fluorocarbons e.g. Teflon ®, polyesters, e.g. polyethylene terephthalate, etc.

As is well known, microwave energy is the electromagnetic wave energy falling in the microwave region of the electromagnetic spectrum. Permitted bands of microwave energy are generally in the range of about 200 to 20,000 megacycles per second with a wavelength ranging from about 13" for the lower frequency to about 0.7" for the highest frequency; narrow bands which find frequent application include frequencies of about 890–940 with a wavelength of about 13″; frequencies of about 2,400–2,500 with a wavelength of about 4–5″, and frequencies of about 17,850 to 18,000 with a wavelength of about 0.7″. However, for the most part, the microwave energies employed will be in the intermediate range of from about 850 to about 3,000, more usually from about 850 to about 950 or 2,000 to about 3,000 megacycles per second. Microwave energy is generated from a suitable high frequency source, such as a Magnetron or Klystron. Various applicators may be employed for providing microwave energy, such as a resonator, wave guide applicator, or standing wave applicator.

The time for the treatment will vary depending upon the degree of disinfection desired. Normally, at least about 1 min. will be required and usually less than about 8 hrs, more usually from about 1 min to 6 hrs, and preferably from about 10 min to 4 hrs. The time will vary with the frequency of the microwave, and the power output of the Magnetron. For the most part, the microwave energy density inside the processing cavity will be up to about 0.025 mW/cm$^3$, and usually above about 0.001 mW/cm$^3$.

It is found, that the protein remains substantially at ambient conditions or mildly elevated temperatures under this treatment, the temperature usually being below about 75° C., more usually below about 60° C., and preferably below about 45° C. That is, there is no substantial temperature increase as determined by a thermocouple applied to the material immediately after subjecting it to exposure to microwaves.

While the combination of dehydrating the protein e.g. lyophilization and exposure to microwaves will normally provide satisfactory decontamination, including sterilization, additional treatment may be employed concurrently or consecutively, such as ultra-violet irradiation, (See U.S. Pat. No. 3,926,556).

In order to demonstrate the subject invention, the following examples were carried out.

EXPERIMENTAL

As an illustrative proteinaceous material a highly purified form of atelopeptide collagen was employed. A description of the material and its preparation may be found in co-pending application Ser. No. 744,536, now U.S. Pat. No. 4,140,537, the appropriate portions of which are incorporated by reference.

In the first experiment, the collagen was homogenized with sterile water to a stock concentration of 34 mg collagen/ml fluid dispersion. Duplicate sets of control specimens and sample specimens were prepared. One ml aliquots were frozen in plastic syringes and lyophilized for 24 hrs at 30° C. at a pressure at 10$^{-4}$ mtorr. Titers were determined before and after lyophilization.

Prior to lyophilization, the collagen solution was inoculated with Pseudomonas spp.; Corynebacterium spp.; Candida spp.; and Staphylococcus spp. to a contamination load of 10$^6$ cfu/ml (cfu—colony forming units). After lyophilization, the load had been reduced to 10$^4$ cfu/ml.

Vegetative organisms were prepared for study by inoculating Trypticase soy broth and incubating overnight.

The microwave cavity was provided by a commercially available microwave oven (Toshiba Model Deluxe 700 oven), which produces a microwave output at 2.45 GHz with an output power of 650 watts. The energy distribution in the cavity was inhomogeneous, so that the samples were subjected to varying amounts of energy, depending upon their position in the cavity.

As a measure of lethal effectiveness of the microwave radiation, a D number was calculated as a function of oven rated power. The D number is defined as the length of radiation exposure time in minutes required to reduce the cfu load by one order of magnitude.

In the first experiment, first group of samples were exposed to 2.4 GHz microwave at 100% power giving a D value of 0.5 min and a second at 50%, power giving a D value of 6.3 min.

To determine the number of surviving microorganisms, serial dilutions were made of each sample to 10$^{-6}$, 0.1 ml was then plated on TSA (Trypticase soy broth agar) and the number of survivors counted.

When the above experiment was repeated employing a collagen solution which had not been inoculated, but was naturally contaminated, after four minutes at full power, there were no survivors.

In the next experiment the effect of the subject treatment on spores was determined. B. subtilis spores in water were employed at a concentration of 10$^6$/ml. A 1 ml aliquot of the spore suspension was lyophilized for 24 hrs and the lyophilized product subjected to 2.45 GHz microwaves at 75% and 100% of the 650 Watt power. After exposure, serial dilutions were made to 10$^{-8}$ and 0.1 ml of each solution plated on TSA and the survivors determined. At 1 hr, there were no survivors, both at 75% and 100% power. However, at 30 min, the D values varied between 3 to 4. This experiment demonstrates that the combination of lyophilization and microwave exposure provides the capability to completely destroy spores under relatively mild conditions.

In the next experiment, the effect of the inhomogeneous field was investigated employing B. subtilis spores 10$^6$/ml which has been lyophilized. Three sets of runs were made with the following protocols. Set 1: 30 min, 100% power, stationary sample; Set 2: 15 min 100% power, 15 min off, stationary sample, 15 min 100% power; Set 3: 15 min 100% power, tubes removed from the oven for 15 min; 15 min at 100% power. For the first two sets, the D values were 17 min and 15 min respectively, while for the third set, the D value was 5.5 min. Furthermore, while there had been a significant reduction of the number of organisms in the first two sets, there was no growth of the samples from the third set.

In the next experiment, an attempt was made to determine the temperature effect of the microwave treatment at full power. Four tubes of lyophilized collagen, containing about 170 grams were introduced into the cavity for a particular time. At the end of the time period, the microwave oven door was opened and a thermocouple probe pushed into the center of the sample and the temperature measured. At 0 time the temperature was 27° C. At 5 min, the temperature varied between 40° and 41° C. At 10 min, the temperature varied between 53° 55° C. At 15 min, the temperature varied between 60° and 65° C. and remained substantially constant till 60 min.

The above results demonstrate that there is an inadequate increase in temperature to provide the observed increase in vegetative organisms reported above.

In order to demonstrate the substantial retention of the physiological properties of the host protein, SDS polyacrylamide gel electrophoresis was employed. Five percent SDS polyacrylamide gel was prepared with 50

μg collagen per gel. The gels were stained with Coomassie brilliant blue and scanned at 560 nm. Alpha, beta and gamma peaks from each scan were cut-out and weighed. Peak areas were normalized to 100% of total. The following table indicates the results, as to collagen without treatment and collagen which is subjected to successive treatment of lyophilization followed by exposure to microwaves.

TABLE I

| Sample Treatment | % α | % β | % λ |
|---|---|---|---|
| Collagen | 44 | 20 | 36 |
|  | 45 | 22 | 33 |
| lyophilized | 37 | 19 | 44 |
|  | 33 | 17 | 49 |
|  | 36 | 16 | 48 |
| · microwave, 30min | 34 | 21 | 45 |
|  | 34 | 19 | 47 |
| · microwave, 60min total | 31 | 17 | 51 |
|  | 36 | 16 | 48 |

It is evident from the above results, that the microwave treatment has no significant effect on the electrophoretic properties of the host protein, so that the structure is substantially retained by the collagen after lyophilization.

Most significantly, the ratios of the peaks, which are indicative of cross-linking, remains substantially constant up to 60 min of microwaving at full power, the primary change being as a result of lyophilization. Also there is no evidence of degradation products.

In the next determination, the solubility of lyophilized collagen was compared with lyophilized collagen which had been microwaved at full power at 30 min and at 60 min, as well as collagen prior to any treatment, by following the concentration of hydroxyproline in solution. 1:50 dilutions of the 34 mg/ml collagen dispersions were made with 1 M acetic acid, the mixture stirred in a refrigerator for 24 hrs, a 1 ml aliquot of the supernatant removed, and the remainder centrifuged at 18,000 rpm for 10 min. The initial 1 ml aliquot and 1 ml of the supernatant after centrifugation was assayed for hydroxyproline to determine the percent solubility of the collagen. Collagen without any treatment was found to have a 96% solubility. Lyophilized collagen was found to have a 72% solubility which remained substantially constant (73, 30 min; 71, 60 min microwave treatment) after microwave treatment.

In order to demonstrate the physiological properties, a series of samples containing about 34 mg of collagen per ml were employed by loading 50 syringes to the 1 ml mark, freezing the syringes, lyophilizing and then exposing 25 of the syringes to 2.45 GHz 650 Watt microwave for 60 min as previously described. Twenty-four each of the treated and untreated syringes were rehydrated to the 1 ml mark with 0.02 M sodium phosphate, 130 mM NaCl, 0.5% lidocaine, the air eliminated, the mixture shaken and the syringe refrigerated.

All syringes were weighed before and after implantation and the total volume of the syringe was implanted in rats at two sites, 2 cc per site, and two animinals for each time point. The time points were 5, 15 and 30 days. At the end of each time, the weight of the explant, and the volume of the explant was determined, as well as the appearance of the explant and surrounding tissue by microscopic and macroscopic observation. There was no evidence of adverse effect on the behavior of the collagen as an implant due to the microwave treatment.

In accordance with the subject invention, a simple, rapid and efficient technique is provided for decontamination, as well as sterilization, of a host protein without adversely affecting the physiological properties of the host protein. The decontamination is achieved by first drying, normally by lyophilization, the host protein to assure the substantial absence of water, followed by treatment of a lethal dosage of microwave radiation for a time sufficient to provide the desired degree of decontamination. The resulting product is decontaminated, usually sterilized, while substantially retaining its physiological properties, retaining substantially the same potency and effectiveness. The method finds wide application with a wide variety of proteins, which because of their physiological applications, must be decontaminated or sterilized, prior to administration to a mammalian host.

Although the foregoing invention has been described in some detail by way of illustration and example for purposes of clarity of understanding, it will be obvious that certain changes and modifications may be practiced within the scope of the appended claims.

What is claimed is:

1. A method for disinfecting a host protein having physiological properties for use in a mammalian host without significantly affecting the physiological, chemical and physical properties of said host protein, said method comprising applying to said host protein substantially freed of water a lethal dosage of microave energy at a temperature above ambient temperature and below about 75° C. and for a time sufficient to decontaminate said host protein.

2. A method according to claim 1, wherein said host protein is dried by lyophilization.

3. A method according to claim 2, wherein said time is in the range of about 1 min to 6 hrs.

4. A method according to claim 3, wherein said microwave energy is in the range of about 850 to 3,000 megacycles per second.

5. A method according to any of claims 1 to 4, wherein said host protein is collagen.

6. A method according to any of claims 1 to 4, wherein said host protein is at least one serum protein.

7. A method for sterilizing a host proteinaceous material for use in a mammlian host obtained as an aqueous dispersion without significantly affecting the physiological, chemical and physical properties of said host protein, said method comprising:

lyophilizing said aqueous dispersion at a temperature below about 50° C. to provide a lyophilized protein product; and irradiating said lyophilized protein product with a lethal dosage of microwave radiation for a time sufficient to sterilize said protein, while maintaining the temperature of said host protein above about ambient and below about 60° C.

8. A method according to claim 7, wherein said protein is collagen.

9. A method according to claim 7, wherein said protein is at least one serum protein.

* * * * *

UNITED STATES PATENT AND TRADEMARK OFFICE
CERTIFICATE OF CORRECTION

PATENT NO. : 4,250,139
DATED : February 10, 1981
INVENTOR(S) : Edward E. Luck and John R. Daniels It is certified that error appears in the above—identified patent and that said Letters Patent is hereby corrected as shown below:

Column 4, line 64, cancel "increase" and substitute therefor --decrease--.

Signed and Sealed this

Eleventh Day of August 1981

[SEAL]

Attest:

Attesting Officer

GERALD J. MOSSINGHOFF
Commissioner of Patents and Trademarks